United States Patent [19]
Wright et al.

[11] Patent Number: 5,605,826
[45] Date of Patent: Feb. 25, 1997

[54] 24 KILODALTON CYTOPLASMIC PROTEASE ACTIVATING DNA FRAGMENTATION IN APOPTOSIS

[75] Inventors: Susan C. Wright, Saratoga; James W. Larrick, Woodside, both of Calif.

[73] Assignee: Panorama Research, Inc., Mountain View, Calif.

[21] Appl. No.: 259,752

[22] Filed: Jun. 10, 1994

[51] Int. Cl.$^6$ ............................ C12N 9/64; C12N 9/50; C07K 1/22
[52] U.S. Cl. ..................... 435/226; 435/212; 435/219; 530/413
[58] Field of Search ................................ 530/350, 413; 435/212, 219, 226; 536/23.2; 424/94.64

[56] References Cited

U.S. PATENT DOCUMENTS

| | | | |
|---|---|---|---|
| 5,298,407 | 3/1994 | Anderson et al. | 435/69.1 |
| 5,340,935 | 8/1994 | Anderson et al. | 536/23.5 |
| 5,360,893 | 11/1994 | Owens et al. | 530/350 |

FOREIGN PATENT DOCUMENTS 93-11246  6/1993  WIPO.

OTHER PUBLICATIONS

Billings, P. C., et al., 1988, Cancer Research 48: 1789–1802.
Wright, S. C., et al., 1993, Journal of Cellular Biochemistry, 53:222–233.
Larrick, J. W., et al., 1990, The FASEB Journal 4:3215–3223.
Yuan, J., et al., 1993, Cell, 75: 641–652.
Stewart, B. W., 1994, Journal of the National Cancer Institute, 86(17): 1286–1296.
Gold, R., et al., 1994, Laboratory Investigation, 71(2):219–225.
Schlegel, J., et al., 1995, FEBS Letters, 364: 139–142.
Zhivotovsky, B., et al., 1994, FEBS Letters, 351: 150–154.
Kwo, P., et al., 1995, The American Journal of Physiology, 268(4Ph 1): G613–G621.
Darmon, A. J., et al., 1994, The Journal of Biological Chemistry 269(51): 32043–32046.
Wang, E., 1995, Cancer Research, 55: 2284–2292.
Heusel, J. W., 1994, Cell, 76(6):977–987.
Miura, M., et al., 1993, Cell, 75: 653–660.
Wright, S. C., et al., 1993, The FASEB Journal, 7(8):1045–1051.
Wright, S. C., et al., 1994, The FASEB Journal, 8(9):654–660.
Wright, S. C., et al., 1994, Journal of Experimental Medicine, 180: 2113–2123.
Sobur, G., et al., 1983, BioTechniques, 1:198–203.
Weaver, V. M., et al., 1993, Biochemistry and Cell Biology 71(9–10): 488–500.
Chundrasekaran, S., et al., 1985, Analytical Biochemistry 150(1): 141–144.
Shi, L., et al., 1992, Journal of Experimental Medicine, 175: 553–566.
Shi, L., et al., 1992, Journal of Experimental Medicine, 176: 1521–1529.
Sarin, A. et al. "Protease Inhibitors Selectively Block T Cell Receptor–triggered Programmed Cell Death in a Murine T Cell Hybridoma and Activated Peripheral T Cells," (1993) The Journal of Experimental Medicine vol. 178 (15) pp. 1693–1700.

(List continued on next page.)

*Primary Examiner*—Robert A. Wax
*Assistant Examiner*—William W. Moore
*Attorney, Agent, or Firm*—Townsend and Townsend and Crew LLP

[57] ABSTRACT

An apoptosis-associated protease having a relative mass of 24 kilodaltons and a defined amino acid composition is disclosed, together with a method for its purification from a cytoplasmic extract of mammalian cells treated with an apoptosis-inducing agent, such as tumor necrosis factor-α or UV irradiation, that comprises affinity chromatography with the serine protease inhibitor DK120 followed by heparin-sepharose chromatography. The protease has activity against the elastase-like substrate MAAPV and is capable of inducing apoptosis in isolated U937 cell target nuclei.

10 Claims, 8 Drawing Sheets

OTHER PUBLICATIONS

Squier, M. et al. "Calpain Activation in Apoptosis," (1994) Journal of Cellular Physiology vol. 159 (2) pp. 229–237.

Green, et al., "Apoptosis and Cancer," PPO Updates, vol. 8, No. 1, Jan. 1994, pp. 1–14.

Wright, et al., "Apoptosis and DNA Fragmentation Precede TNF–Induced Cytolysis in U937 Cells," J. of Cellular Biochem., 48:344–355 (1992).

Gerschenson, et al., "Apoptosis: A Different Type of Cell Death," The FASEB Journal, vol. 6, Apr. 1992, pp. 2450–2455.

Schwartzman, et al., "Inernucleosomal Deoxyribonucleic Acid Cleavage Activity in Apoptotic Tymocytes: Detection and Endocrine Regulation," Endocrinology, vol. 128, No. 2, pp. 1190–1197 (1991).

Duvall, et al., "Death and the Cell," Immunology Today, vol. 7, No. 4, 1986, pp. 115–119.

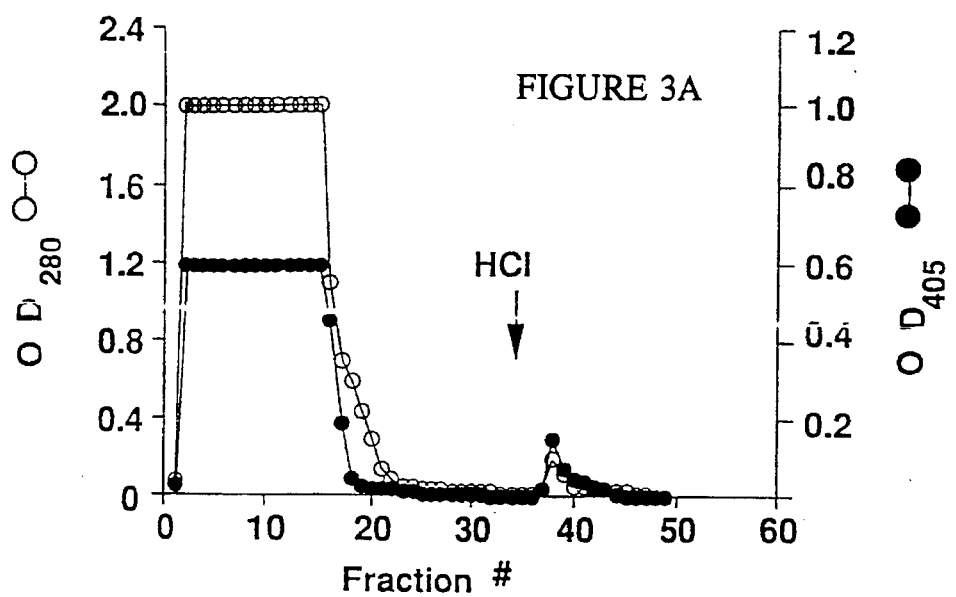
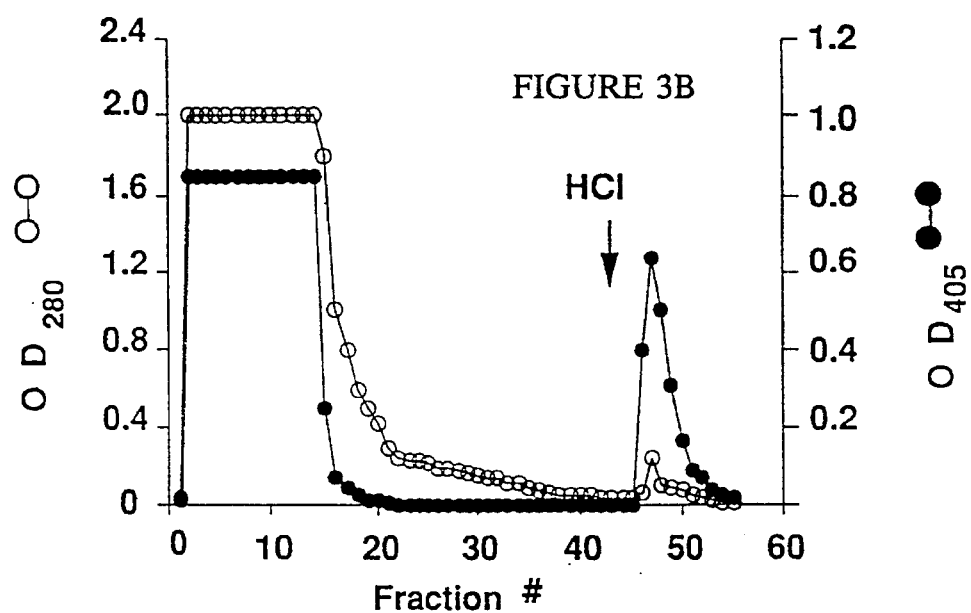
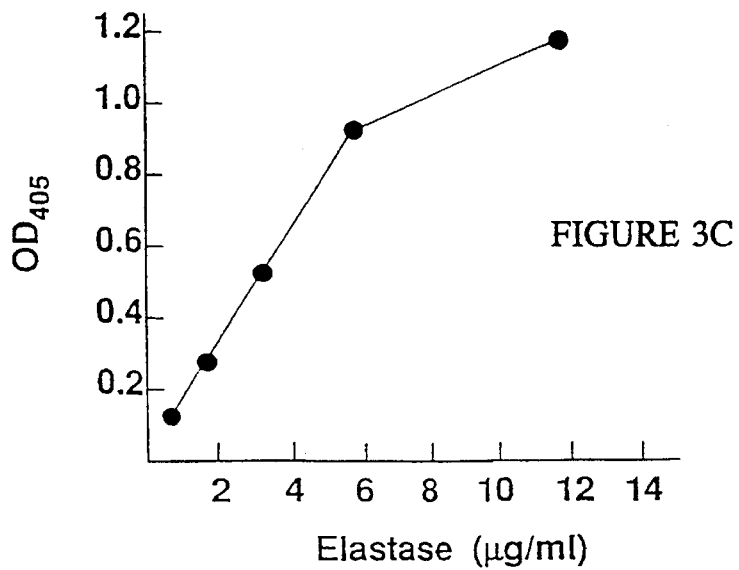

U937 Control

U937 + UV Light

24 KILODALTON CYTOPLASMIC PROTEASE ACTIVATING DNA FRAGMENTATION IN APOPTOSIS

FIELD OF THE INVENTION

The present invention relates to proteases involved in apoptosis signalling pathways, to processes for the purification of the proteases, and more particularly to methods for the use of the proteases to modulate apoptosis in target cells.

BACKGROUND OF THE INVENTION

Necrosis and apoptosis are two distinct modes of death for nucleated eukaryotic cells. Necrosis may occur as a result of cellular injury, typically complement attack, lytic viral infection, toxins and the like. Apoptosis or "programmed cell death", on the other hand, is the physiological process of cell death that functions to control cell populations during embryogenesis, immune responses, hormone withdrawal from dependent tissues, normal tissue homeostasis, and regressing tumors, as described in Duvall, E., et al. (1986) *Immunol. Today* 7, 115–119; Walker, N. I., et al. (1988) *Meth. Achiev. Exp. Pathol.* 13, 18–54; and Gerschenson, L. E. et al. (1992) *FASEB J.* 6, 2450–2455. Unlike cellular necrosis, apoptotic cytolysis is not usually associated with cellular injury. Apoptosis may be induced by immunologically mediated methods, such as antibody dependent cell cytotoxicity (K cell attack), viral infection, and attack by cytotoxic T lymphocyte effector cells, lymphotoxins, or natural killer (NK) cells. Further, apoptosis may be induced in tumor cells by a variety of physical, chemical, and biochemical apoptosis inducing agents, including gamma radiation, UV light, heat shock, cold shock, cisplatin, etoposide, teniposides, DNA alkylating agents, macromolecular synthesis inhibitors, and the like.

Cytological and biochemical changes are associated with the cellular apoptotic process. The cytoplasm condenses, and the endoplasmic reticulum dilates to form vesicles which fuse with the cell membrane, producing characteristic cellular morphology. Changes in the nuclei include the formation of dense crescent shaped aggregates of chromatin, nucleolus fragmentation, and formation of vesicles at or on the nuclear membrane. During apoptosis endonucleases present in the cell cut the DNA in the linker regions between nucleosomes to release DNA fragments in integer multiples of 180–190 base pairs, Cohen J. J., et al. (1984) *J. Immunol.* 132, 38–42. The pattern of cleavage is believed to result from the vulnerability of the linker DNA between the nucleosomes to endonucleases.

However, the identification of the relevant nucleases involved in apoptosis has not yet been achieved. Similarly, the elucidation of the cellular signalling transduction mechanisms beginning with the apoptosis inducing agent and leading to endonuclease activation have not been determined.

Therefore, it would be useful to provide compositions and methods for modulating cell growth and proliferation by regulation of the apoptotic signalling pathway. The compositions would have particular therapeutic utility where cell growth or proliferation is aberrant, for example, as antineoplastic agents. The present invention solves these and other related needs.

SUMMARY OF THE INVENTION

The present invention describes a mammalian protease capable of inducing apoptotic DNA fragmentation. The protease is found in elevated levels in mammalian tumor cells treated with apoptosis inducing agents. The protease has activity against an elastase like substrate MAAPV.

According to one aspect of the invention, there is provided a pharmaceutical composition for the modulation of cell growth and proliferation, the composition comprising a 24 kDa protease and a pharmaceutically acceptable carrier therefore.

In another aspect of the invention, there is provided a process for isolating and purifying an apoptotic protease from mammalian cells, the process comprising the steps of preparing a cytoplasmic extract of mammalian cells, applying the extract to an affinity column having an immobilized protease inhibitor, eluting a protease containing fraction from the affinity column, and enriching the protease containing fraction to obtain a substantially pure apoptotic protease. In some aspects of the invention, the protease inhibitor is a serine protease inhibitor, for example, DK 120. The invention also includes a nucleic acid encoding the protease of the invention, vectors containing the nucleic acid sequences, and cells transformed with the nucleic acid sequences.

BRIEF DESCRIPTION OF THE DRAWINGS

FIG. 1 comprises FIG. 1A and FIG. 1B and shows the inhibition of DNA fragmentation induced by TNF and UV light by serine protease inhibitors.

In FIG. 2, U937 cells were pretreated with and without TPCK 10 μM for 30 min, exposed to UV light 0.15 J/cm$^2$, incubated another 2.5 h, then the DNA extracted and analyzed by agarose gel electrophoresis. Lane 1 of FIG. 2 contains molecular weight markers, lane 2 contains untreated U937, lane 3 contains U937 treated with TPCK, lane 4 contains U937 treated with UV light, lane 5 contains U937 treated with TPCK and UV light.

FIG. 3 comprises FIGS. 3A, 3B, and 3C, and shows the DK120 affinity purification of the 24 kDa U937 protease. OD measured at 280 nm reflects total protein content, whereas OD at 405 nm measures protease activity on the MAAPV substrate. FIG. 3A shows the OD of cell lysates from normal U937 cells, and FIG. 3B shows the OD of cell lysates from UV-light pretreated cells. FIG. 3C shows a leukocyte elastase dose response curve, in which each fraction was assayed for protease activity against the MAAPV substrate.

FIG. 4 comprises FIG. 4A and FIG. 4B and shows a kinetic protease assay to quantitate DK120-binding protease activity against the MAAPV substrate.

FIG. 6 comprises FIG. 6A and FIG. 6B and shows activation of DNA fragmentation in isolated nuclei by semi-purified protease fractions.

DESCRIPTION OF THE PREFERRED EMBODIMENT

Definitions

Figure 1A:
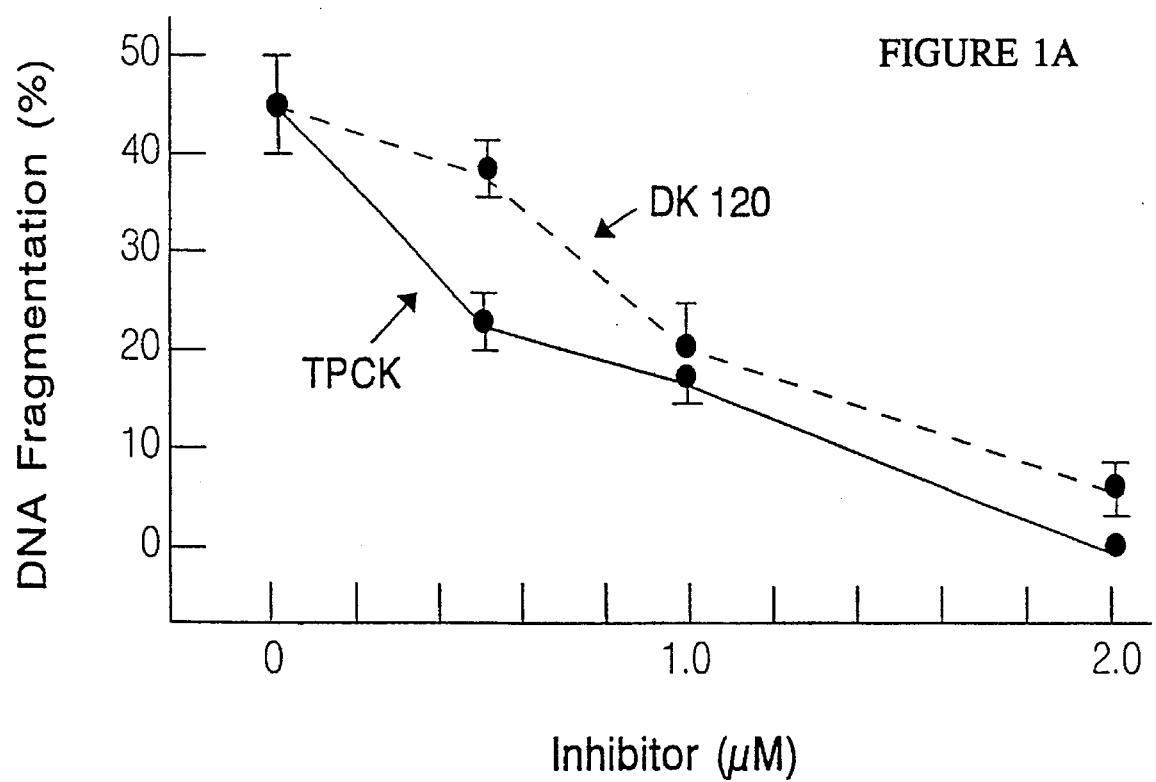
FIG. 1A shows the fragmentation inhibition of DK120 (carbobenzoxy-ala-ala-borophe) and TPCK to TNF.

Generally, the nomenclature used hereafter, and the laboratory procedures in cell culture and protein biochemistry are those well known and commonly employed in the art. Generally, enzymatic reactions and column chromatography are performed according the manufacturer's specifications. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below.

The terms "therapeutically effective level" or "therapeutically effective dose" as used herein mean the minimum blood level of drug required to achieve a therapeutic effect. The terms "prophylactically effective dose" or "prophylactically effective level" as used herein mean the minimum blood level of drug required to achieve a prophylactic effect. In prophylactic applications, compositions containing the compounds of the invention are administered to a patient susceptible to or otherwise at risk of a particular disease. In therapeutic applications, compositions are administered to a patient already suffering from a disease, in an amount sufficient to cure, ameliorate, or at least partially arrest the symptoms of the disease, or complications arising therefrom.

The terms "pharmaceutically acceptable" or "therapeutically acceptable" refer to a substance which does not interfere with the effectiveness or the biological activity of the active ingredients and which is not toxic to the host or the patient.

The terms "encoding" or "encodes" refer generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g. Watson et al., (1987) *The Molecular Biology of the Gene*, (4th Edition), Vols. 1 & 2, Benjamin, Menlo Park, Calif.

As used to refer to nucleic acid sequences, the term "homologous" indicates that two or more nucleotide sequences share a majority of their sequence. Generally, this will be at least about 70% of their sequence and preferably at least 95% of their sequence. Another indication that sequences are substantially identical is if they hybridize to the same nucleotide sequence under stringent conditions (see, e.g., Sambrook et al., *Molecular Cloning-A Laboratory Manual*, Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins or polypeptides, the term "homologous" is meant to indicate two proteins or polypeptides share a majority of their amino acid sequences. Generally, this will be at least 90% and usually more than about 95%. Homology for polypeptides or proteins is typically measured using sequence analysis software, see e.g. Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, and other modifications. Conservative substitutions typically include substitutions within the following groups glycine, alanine; valine, isoleucine, leucien; aspartic acid, glutamic acid; asparagine, glutamine; serine, threonine; lysine, arginine; and phenylalanine, tyrosine.

The term "isolated" as applied to nucleic acids, means a nucleic acid substantially separated from other macromolecules, cellular components, or DNA sequences which naturally accompany a native nucleic acid, e.g. ribosomes, polymerases, other nucleic acid sequences, and the like. The term includes a nucleic acid that has been removed from its naturally occurring environment, and includes recombinant or cloned DNA isolates and chemically synthesized analogues, and analogues biologically synthesized by heterologous systems. A substantially pure or biologically pure nucleic acid includes isolated forms of the nucleic acid.

The phrase "biologically pure" or "substantially pure" refers to material that is substantially or essentially free from components which normally accompany it as found in its native state.

The term "recombinant" refers to a nucleic acid sequence which is not naturally occurring, or is made by the artificial combination of two otherwise separated segments of sequence, i.e. by chemical synthesis, genetic engineering, and the like.

The present invention examines the role of proteases in signal transduction leading to DNA fragmentation and apoptosis. It has been surprisingly discovered that certain inhibitors of serine proteases block TNF or UV light-induced apoptosis in tumor cell lines. A 24 kDa protease has been purified that was activated by UV light in U937 cells and induced DNA fragmentation in isolated nuclei.

The intracellular apoptotic events and mechanism may differ depending on the cell type and inducing agent. Some examples of apoptosis require new gene expression and protein synthesis, as described for example, in Cohen J. J., et al. (1984) *J. Immunol.* 132, 38–42, Ucker, D. S., et al. (1989) *J. Immunol.* 143, 3461–3469, and Sellins, K. S., et al. (1987) *J. Immunol.* 139, 3199–3209. In other apoptotic examples, gene expression and protein synthesis are not required, as described in Duke, R. C., et al., (1983) *Proc. Natl. Acad. Sci.* 80, 6361–6365, and Martin, S. J., et al. (1990) *J. Immunol.* 145, 1859–1867. Differences have also been reported in the requirement for extracellular calcium, Cohen J. J., et al., (1984) *J. Immunol.* 132, 38–42; Kyprianou, N., et al., (1988) *Prostate* 13, 103–117; McConkey, D. J., et al., (1990) *FASEB J.* 4, 2661–2664; and Alnemri, E. S., et al., *J. Biol. Chem.* 265, 17323–17333.

Both TNF and UV light act as apoptosis inducing agents in many cell types and suggest that both agents stimulate signals converging to a final common pathway leading to DNA fragmentation. This process does not require protein synthesis or extracellular calcium, Hasegawa, Y., et al. (1989) *J. Immunol.* 142, 2670–2676. Phorbol myristate acetate (PMA) inhibits apoptosis induced by TNF or UV light, suggesting a regulatory role for PKC, in agreement with other examples of apoptosis described in Kanter, P., et al., (1984) *Biochem. Biophys. Res. Commun.* 118, 392–399; Rodriguez-Tarduchy, G., et al. (1989) *Biochem. Biophys. Res. Commun.* 164, 1069–1075; Lucas, M., et al. (1990) *FEBS Lett.* 279, 19–20; McConkey, D.J., et al. (1989) *J. Biol. Chem.* 264, 13399–13402; and McConkey, D. J., et al. (1991) *J. Immunol.* 146, 1072–1076.

Augmentation of Intracellular Protein phosphorylation by inhibitors of serine/threonine-dependent phosphatases promoted TNF-induced apoptosis and overcame the resistance of a variant of the human histiocytic lymphoma cell line U937, as described in Wright, S. C., et al. (1993) *J. Cell. Biochem.* 53: 222–233, suggesting a critical role for protein kinases in signal transduction, although no specific kinase has been identified.

Apoptosis in U937 cells is also blocked by 3-aminobenzamide, an inhibitor of poly ADP-ribose polymerase (pADPRp). Furthermore, increased levels of pADPRp activity have been measured in lysates of TNF or UV light-treated U937 cells. These findings are in agreement with other reports of activation of pADPRp in cells in response to TNF, as described in Agarwal, S., et al. (1988) *J. Immunol.* 140, 4187–4192. Whether this enzyme functions to activate endonucleases or contributes to cell death through depletion of NAD, as described in Berger, N. A., (1985) *Radiation Research* 101 4–15, and Carson, D.A., et al. (1986) *Exp. Cell. Res.* 164 273–281, has not yet been established.

The present invention provides a protease which is involved in the apoptotic signalling pathway in human U937 tumor cells. Two inhibitors of serine proteases, TPCK and DK120, suppressed DNA fragmentation in the U937 histiocytic lymphoma in response to either TNF or UV light as well as UV light-induced DNA fragmentation in the BT-20 breast carcinoma, HL-60 myelocytic leukemia, and 3T3 fibroblasts. The protease was purified by affinity chromatography with DK120 as ligand and showed high activity on a synthetic substrate preferred by elastase-like enzymes (ala-ala-pro-val), but showed little or no activity against a trypsin substrate, BLT, or a chymotrypsin substrate, ala-ala-pro-phe-pNa. Induction of apoptosis correlated with a 10 fold increase in the activity of the DK120-binding protease purified from UV-treated U937 as compared to recovery from normal cells. Further purification to homogeneity by subsequent heparin-Sepharose affinity chromatography followed by reverse phase HPLC revealed a single band of 24 kDa on a silver stained SDS gel. In addition to protease activity, the purified enzyme induced DNA fragmentation in isolated U937 nuclei. Thus, the 24 kDa protease transmits signals leading to DNA fragmentation in U937 cells undergoing apoptosis.

Thus, the present invention provides a protease having a role in the signaling pathways leading to apoptosis. The role of the protease was observed by testing the effects of a variety of protease inhibitors on DNA fragmentation induced by TNF or UV light in an apoptotic cell line. The regulation and modulation of apoptosis was examined using primarily the human histiocytic lymphoma cell line U937 as a model system. This cell line undergoes apoptosis in response to a variety of apoptotic inducing agents, including tumor necrosis factor alpha (TNF), UV light, heat shock, oxidative stress, and chemotherapeutic drugs, as described in Wright, S. C., et al. (1992) *J. Cell. Biochem.* 48, 344–355, Wright, S. C., et al. (1993) *FASEB J.* 7, 1045–1051. As used herein, "apoptosis inducing agent" includes any biological, chemical, biochemical or physical means of inducing a complete or partial apoptotic response in a target cell. Target cells may be normal cells, or cells having aberrant growth or proliferation, such as tumor cells. Most nucleated eukaryotic cells tested have shown the capacity to undergo apoptosis in response to appropriate stimuli, including non-mammalian cells such as avian and nematode. An analogous process has not been demonstrated in prokaryotes.

Examples of apoptosis inducing agents include UV light, hyperthermia or heat shock, calcium, ATP, actinomycin D, A23187 $Ca^{2+}$-$Mg^{2+}$ ionophore, cytochalasin B, cycloheximide, anti-CD3/T-cell receptor antibodies, epipodophyllotoxins, gliotoxin, glucocorticoids, lymphotoxins, RU486, TCDD, TGF-β1, oxidative stress, viral infections, chemotherapeutic drugs, cold shock, gamma radiation, cisplatin, etoposide, teniposides, DNA alkylating agents, macromolecular synthesis inhibitors, immunological agents such as natural killer cells, effector cells, lymphotoxins, K cells, T cells, and the like, and others, as described for example in Green, D. R. et al., *Apoptosis and Cancer*, in Principles and Practice of Oncology Updates Volume 8, J. B. Lippincott Company, January 1994 Number 1, and Gerschenson, L. E., et al. (1992) *FASEB J.* 6:2450–2455.

Figure 1B:
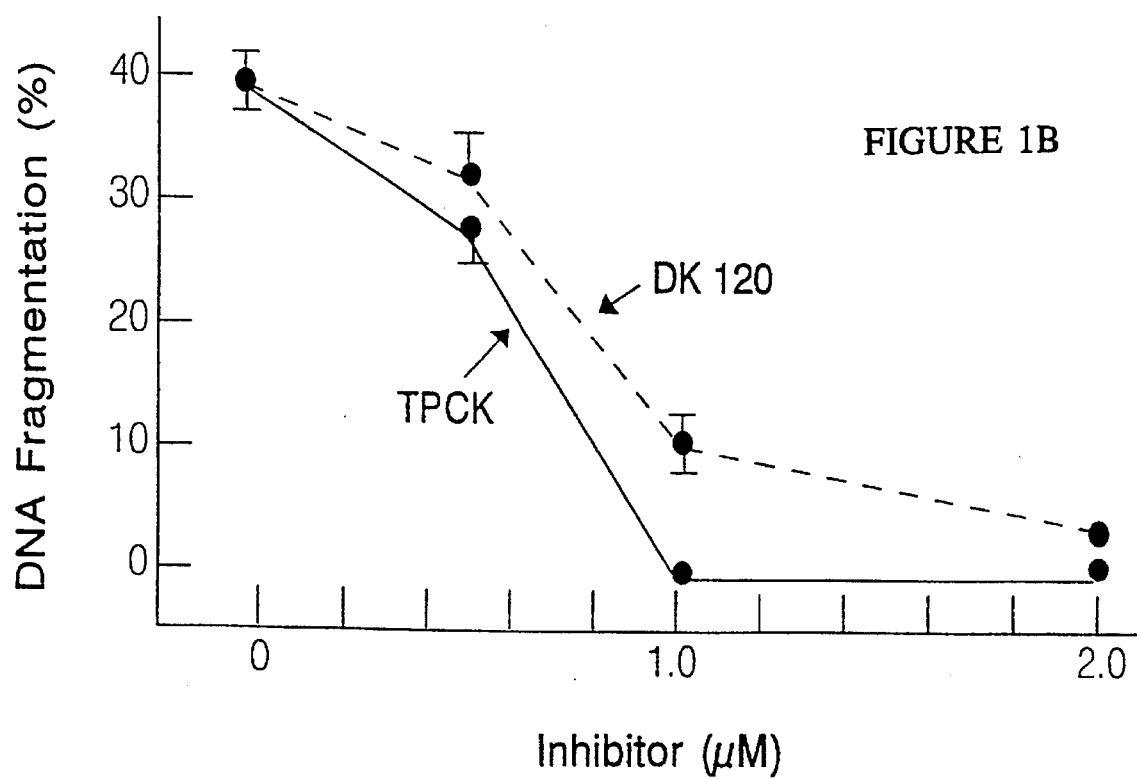
FIG. 1B shows the fragmentation inhibition of DK120 and TPCK to UV light.

Two serine protease inhibitors, TPCK and DK120, have been found to be especially potent inhibitors of apoptotic DNA fragmentation, as shown in FIG. 1. U937 cells were pretreated with the indicated concentrations of inhibitors for 1 hr, then exposed to either TNF 1.0 ng/ml plus cycloheximide 0.5 μg/ml (FIG. 1A) or UV light at 0.1 $J/cm^2$ (FIG. 1B), dosages in the linear portion of the dose response curve. After incubating for 1.5–2 h, assays were harvested and % DNA fragmentation was determined. As seen in FIG. 1, both DK120 and TPCK could dose-dependently inhibit DNA fragmentation with maximum suppression occurring at 2.0 μM in this experiment. TPCK is a potent inhibitor of chymotrypsin-like enzymes, whereas DK120 is a boronic acid-containing tripeptide substrate analog that also potently inhibits chymotrypsin-like enzymes, Kinder, D. H., et al. (1985) *J. Med. Chem.* 28, 1917–1925, and Kinder, D. H. et al. (1991) *Invasion and Metastasis* 12:309–319.

Figure 2:
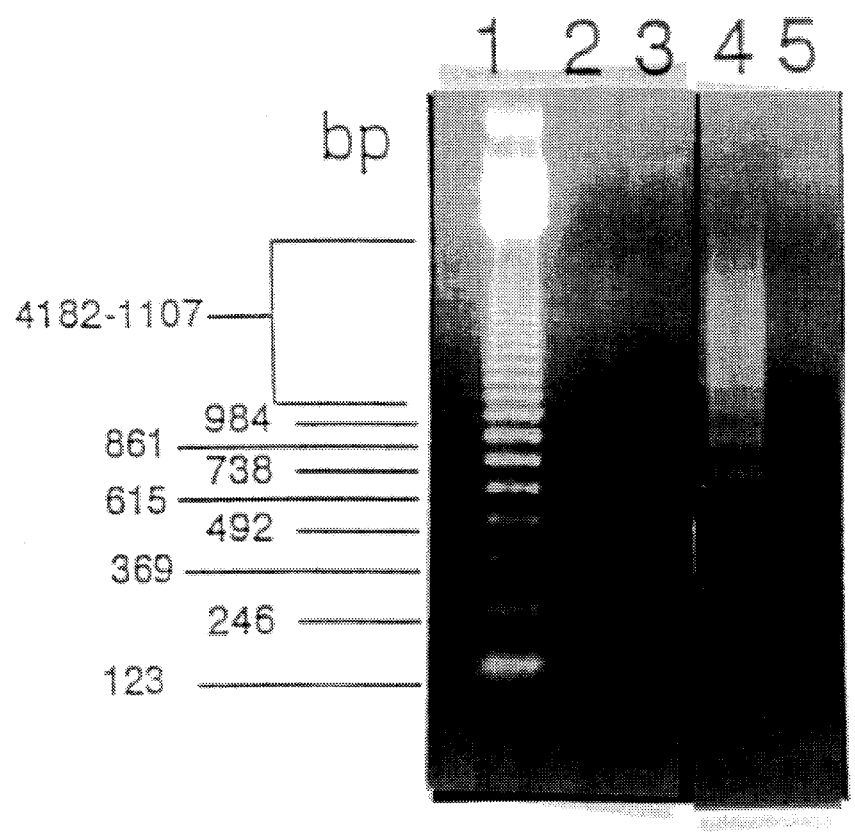
FIG. 2 shows the inhibition of DNA fragmentation by TPCK as shown by agarose gel electrophoresis.

Inhibition of apoptotic DNA fragmentation by TPCK was confirmed by agarose gel electrophoresis as shown in FIG. 2. DNA from untreated U937 cells (lane 2) or cells treated with TPCK alone (lane 3) showed no DNA fragments. Exposure of U937 cells to UV light resulted in the appearance of DNA fragments in multiples of 180 base pairs, typical of apoptosis (lane 4). However, pretreatment with TPCK completely abolished UV light-induced DNA fragmentation (lane 5).

To further characterize the protease activity involved in apoptosis, the effects of a panel of compounds on both TNF and UV light-induced apoptosis of U937 cells was tested. All compounds were used at nontoxic concentrations for the duration of the assay as determined by trypan blue exclusion. The $IC_{50}$ values of active inhibitors as well as the highest nontoxic concentration of inactive compounds tested are provided in Table 1.

TABLE 1

Effect of Protease Inhibitors on TNF and UV-Light Induced Apoptosis

| Inhibitor | Target Protease | Active Concentration | Inactive Compounds Highest Concentration Tested |
|---|---|---|---|
| TPCK (N-1-tosylamide - 2-phenylethylchloromethyl ketone) | Serine/Chymotrypsin | 2.0 µM | |
| APNE (N-acetyl-DL-Phenylalanine β-naphthyl ester) | Chymotrypsin | 40 µM | |
| DK120 | Serine/Chymotrypsin | 1.2 µM | |
| IBA (isopropylboronic acid) | None | | 20 µM |
| TLCK (N-α-p-tosyl-L-lysine-chloromethyl ketone) | Serine/Trypsin | | 50 µM |
| TAME (p-toluene-sulfonyl-L-arginine methyl ester) | Trypsin | | 100 µM |
| PMSF (phenylmethylsulfonylfluoride) | Serine | | 100 µM |
| Chymostatin | Serine | | 100 µM |
| DFP (diisopropylfluorophosphate) | Serine | | 100 µM |
| Benzamidine | Serine | | 100 µM |
| Leupeptin | Serine Some cysteine | | 100 µM |
| E64 | Cysteine | | 100 µM |
| N-ethylmaleimide | Cysteine | | 20 µM |
| Bestatin | Aminopeptidase | | 100 µM |

In addition to TPCK and DK120, APNE, a chymotrypsin pseudosubstrate, also blocked DNA fragmentation. However, not all inhibitors of serine proteases were active since TLCK, TAME, PMSF, chymostatin, DFP, benzamide, and leupeptin were without effect. IBA is a boronic acid analog devoid of protease inhibitory activity which does not inhibit DNA fragmentation, indicating that the inhibition by DK120 is not a nonspecific effect of any boron compound. In addition, the inhibitors of sulfhydryl dependent enzymes, E64 and N-ethylmaleimide, and the aminopeptidase inhibitor, bestatin, were inactive. Negative results may be inconclusive since they may be due to a) inefficient penetration of the inhibitor to the presumably intracellular site of protease action or b) cellular toxicity at effective inhibitor concentrations.

To determine if these findings were unique to U937 or if other cell lines also require protease activity to undergo apoptosis, the effects of several inhibitors on apoptosis induced by UV light in the human mammary carcinoma, BT-20, the murine fibroblast cell line, 3T3, and the human myeloid leukemia, HL-60 were tested. For the BT-20 and 3T3 cells, target cells were pretreated for one hour (with or without inhibitors as indicated in the table) and exposed to UV light at 0.5 $J/cm^2$ and then incubated for eight hours prior to assessing DNA fragmentation. HL-60 cells were pretreated for one hour (with or without inhibitors as indicated in the table) and exposed to UV at 0.2 $J/cm^2$ and then incubated for two hours prior to assessing DNA fragmentation.

TABLE 2

Inhibition of DNA Fragmentation by Protease Inhibitors in Several Tumor Cell Lines

| | Target Cells | | |
|---|---|---|---|
| Inhibitor | BT-20 | 3T3 | HL-60 |
| — | 44 ± 3.6 | 38 ± 1.9 | 49 ± 2.0 |
| TPCK 5 µM | 0 ± 0 | 18 ± 0.8 | 1 ± 2.3 |
| TPCK 11 µM | 19 ± 5.5 | 32 ± 1.1 | 19 ± 2.0 |
| DK 120 5 µM | 0 | 19 ± 1.9 | |
| DK 120 1 µM | 0 | 24 ± 0.3 | |
| DK 120 0.2 µM | 5 ± 8.7 | | |
| DFP 100 µM | 43 ± 1.9 | | |
| E64 100 µM | 41 ± 5.6 | 42 ± 2.7 | |
| Leupeptin 100 µM | 42 ± 5.6 | 36 ± 2.6 | |

Table 2 shows that both TPCK and DK120 effectively blocked DNA fragmentation, whereas DFP, E64, and leupeptin were inactive. Taken together, these results indicate that the activity of a serine protease is essential for at least one apoptotic pathway operating in different cell types responding to different stimuli.

To purify the apoptotic protease, a DK120 affinity column was prepared. The matrix efficiently bound commercially available chymotrypsin, which could be eluted with 0.1M HCl. After neutralization, the eluted material still exhibited high levels of protease activity measured on the SAAPP substrate.

To prepare starting material, U937 cells were exposed to UV light (0.2 J/cm$^2$) and incubated at 37° C. until approximately 50–70% of the cells exhibited the apoptotic morphology (this usually required 1.5–2 hr. incubation). Numerous cytoplasmic membrane blebs characteristic of apoptosis were easily discernable by light microscopy, see Wright, S. C., et al. (1992) *J. Cell. Biochem.* 48, 344–355. Cells were harvested at this time point while they were ≧95% viable by trypan blue exclusion. However, 90–100% of the cells were destined to die if the incubation was continued another 2–3 hr. Cytoplasmic extracts were prepared from apoptotic as well as normal untreated U937 cells. Material from equal numbers of control and UV light treated cells containing equal amounts of protein were chromatographed in an identical fashion on DK120 affinity columns. The results in FIG. 3 show the vast majority of the protein as detected by absorption at 280 nm passed through the column in the unbound fractions #2–17, whereas a relatively small amount of material eluted with 0.1M HCl. Proteolytic activity present in the eluted fractions was tested using several different synthetic substrates. The eluate from UV irradiated cells showed high proteolytic activity against the elastase substrate methoxysuccinyl-ala-ala-pro-val- p-nitroanilide (MAAPV), but relatively low activity against the chymotrypsin substrate succinyl-ala-ala-pro-phe-p-nitroanilide (SAAPP), or the trypsin substrate, N-α-benzyloxycarbonyl-L-lysine thiobenzyl ester (BLT). The eluate from the control cells showed low activity against all three substrates. Therefore, proteolytic activity was monitored during protein purification using the MAAPV substrate. To maximize sensitivity, this assay was carried out at room temperature for 20 hr. However, the dose response using commercially available leukocyte elastase was still linear up to an OD of 1.0 even at this prolonged incubation time (FIG. 3C).

The profiles of protease activity tested in all the column fractions demonstrate high levels of activity in the unbound fractions. However, when the flow-through fractions were pooled and re-applied to the DK120 column, all protease activity was still found in the unbound fractions and not in the eluate. Thus, lysates from both control and UV treated U937 cells contain substantial amounts of proteases that do not bind to the DK120 column.

Figure 4A:
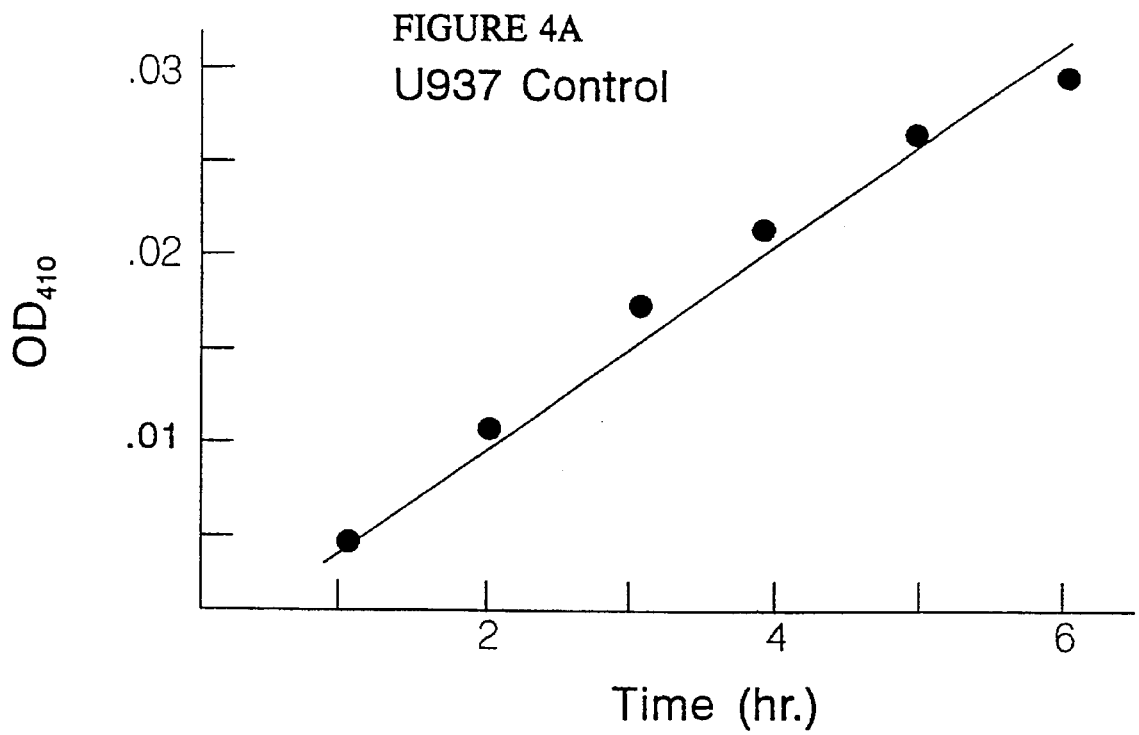
FIG. 4A shows active fractions of protease purified from normal U937 cells.
Figure 4B:
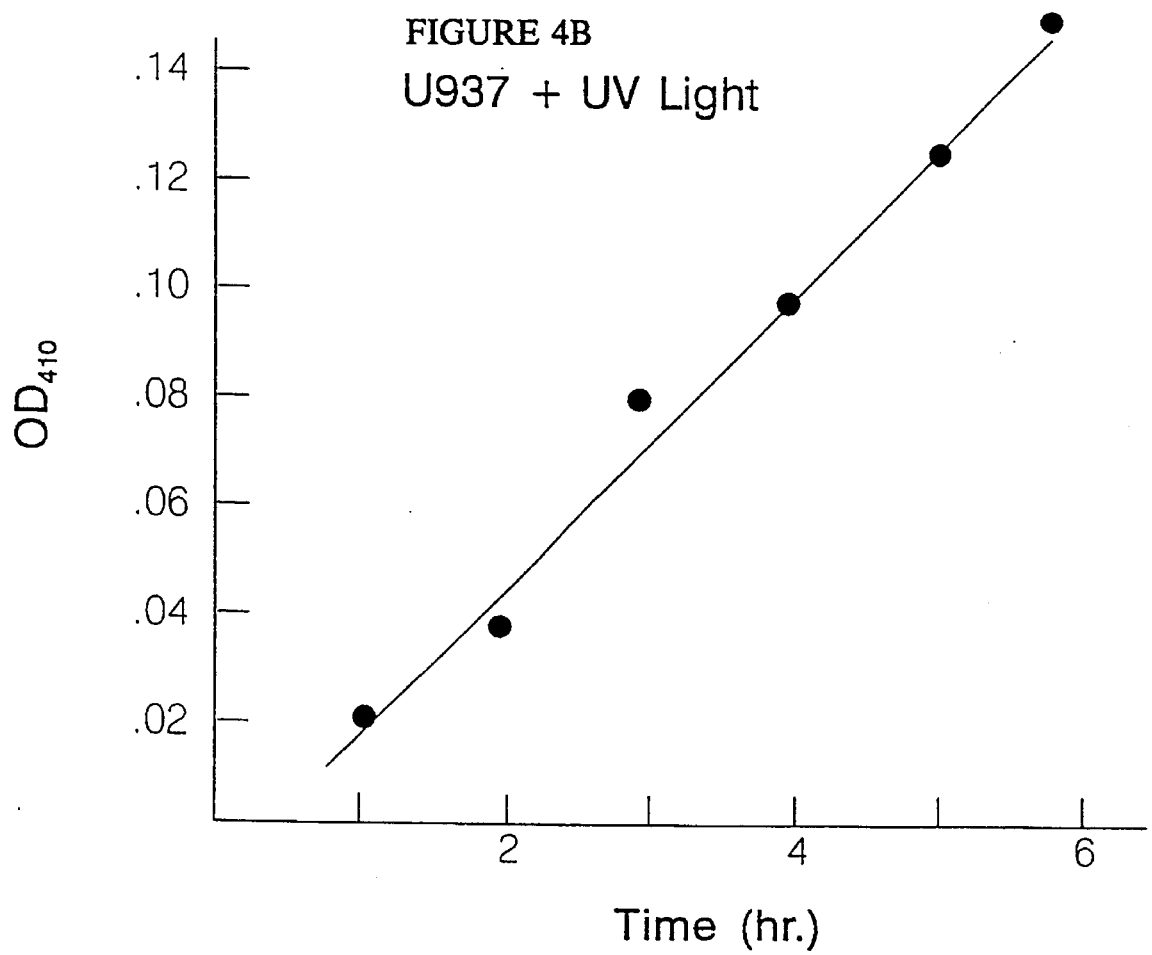
FIG. 4B shows active fractions of protease purified from UV light treated U937 cells.

The protease activity profiles suggest that enzyme activity in the eluate from UV treated cells is significantly increased over that recovered from control cells. To quantitate activity, the active eluted fractions from each column were pooled separately and tested in a kinetic assay. The results in FIG. 4 show a linear increase in optical density monitored from 1–6 hr. Units of enzyme activity calculated as described in Example 6 revealed a total recovery of 27.8 U from control cells versus 248 U from UV treated cells. These results indicate that UV treatment causes almost a 10 fold increase in the activity of DK120-binding enzymes. No UV-activated protease could be isolated from Sepharose 6B control columns, indicating that this enzyme does not nonspecifically bind to the unconjugated resin.

Figure 5:
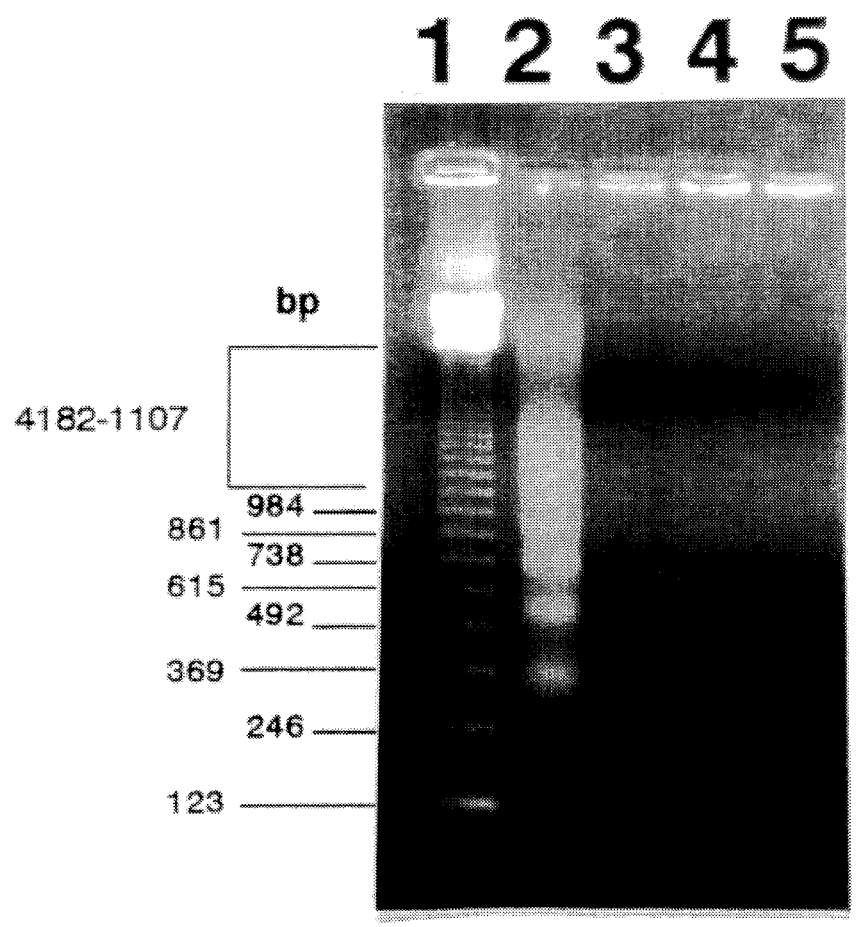
FIG. 5 shows the visualization of DNA fragmentation by endonuclease activity in isolated nuclei. Lane 2 shows apoptotic DNA fragmentation in response to incubation with the protease of the present invention. The sample of Lane 3 was pre-treated with alpha1-anti-protease. Lane 4 and 5 show the DNA treated with alpha1-anti-protease alone, or untreated, respectively. Size markers (in base pairs) are provided in lane 1.

Gel electrophoresis was employed to test the ability of the semi-purified protease to generate apoptotic endonuclease DNA cleavage. During apoptosis, endonucleases cleave DNA in the linker regions to release fragments in multiples of 180 base pairs. DNA was extracted from isolated nuclei after exposure to DK120 affinity-purified protease obtained from U937 cells exposed to UV light. The results in FIG. 5 show that isolated nuclei incubated with the semi-purified protease released internucleosomal-sized DNA fragments to produce the electrophoretic "ladder" pattern typical of apoptosis (FIG. 5, lane 2). However, if the protease preparation was pretreated with α1-anti-protease for 1 hr. prior to adding to the nuclei, DNA fragmentation was abolished (FIG. 5, lane 3). The DNA from untreated nuclei (lane 5) or from nuclei treated with α1-anti-protease alone (lane 4) remained in high molecular weight form. These results confirm that a DK120-binding protease can activate internucleosomal DNA cleavage in isolated U937 nuclei.

Figure 6A:
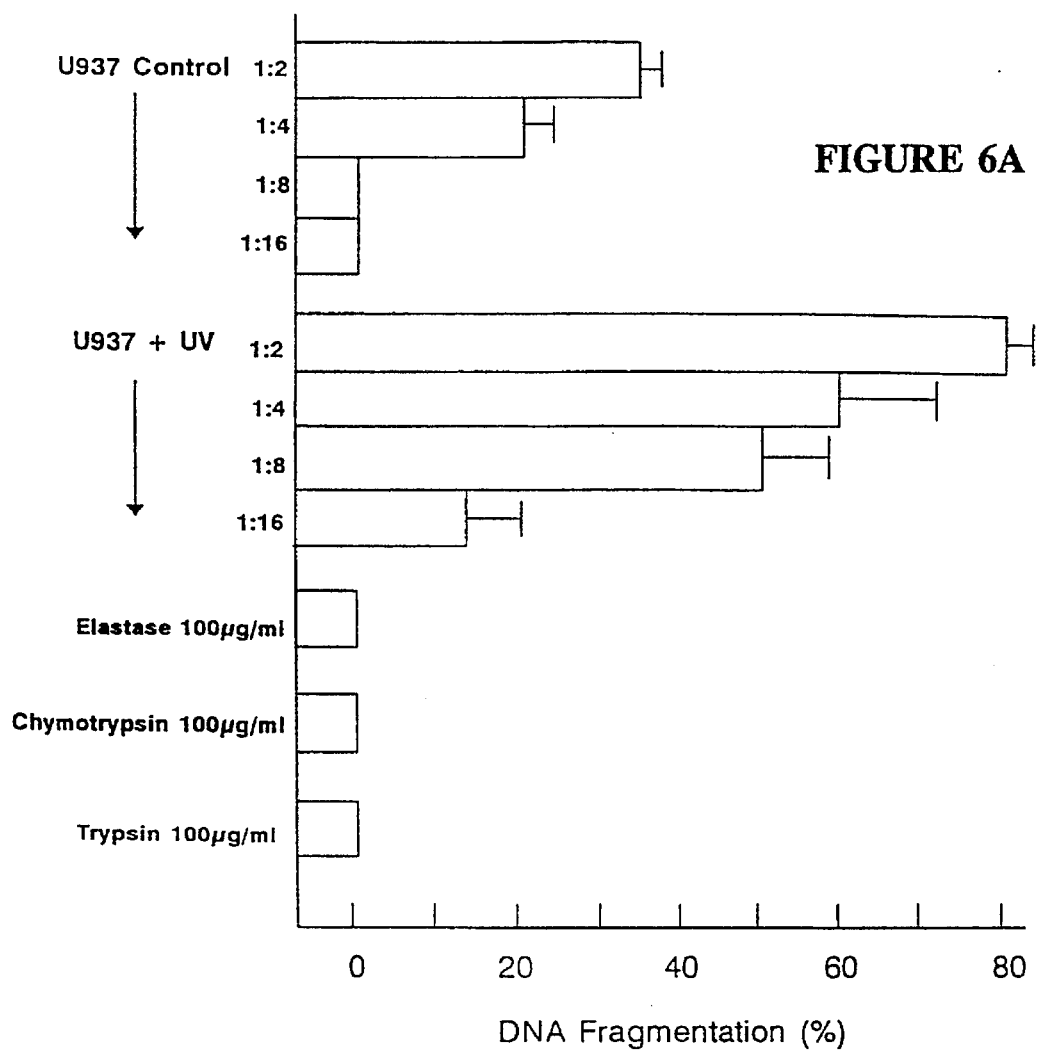
FIG. 6A shows % DNA fragmentation by pooled protease preparations in U937 nuclei, together with commercially available proteases.
Figure 6B:
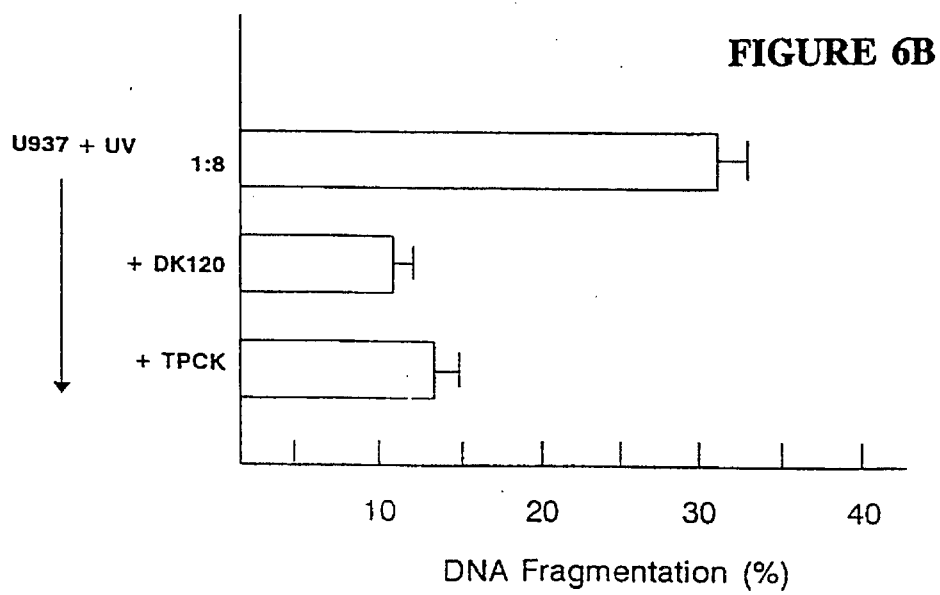
FIG. 6B shows the % DNA fragmentation by the protease pool isolated from UV-treated cells, in the presence of 50 μM of protease inhibitors TPCK and DK120.

To further examine their role in apoptosis, the two pools of semi-purified protease were tested for their effects on isolated U937 nuclei. The results in FIG. 6A show that both pools caused DNA fragmentation, although the pool derived from UV treated cells had much higher activity than that from control cells. In contrast, elastase, chymotrypsin, and trypsin tested at concentrations as high as 0.1 mg/ml were completely inactive. Furthermore, the nuclear DNA fragmenting activity of protease isolated from UV-treated cells was inhibited by DK120 and TPCK, as shown in FIG. 6B. This suggests that the semi-purified protease may directly or indirectly activate a nuclease endogenous to U937 nuclei. Alternatively, the protease may modify chromatin structure to make the DNA more susceptible to digestion by a nuclease that may contaminate the protease preparation. This possibility was tested by incubating both pools with naked DNA isolated from U937 cells. DNase activity was measured using purified U937 DNA as a substrate as described in Example 5.

TABLE 3

Semi-Purified Protease Preparations Do Not Have DNase Activity

| Sample | % DNA Fragmentation |
|---|---|
| U937 Control Protease | 0 |
| UV-Activated U937 Protease | 0 |
| DNase 1 1.0 ng/ml | 61 |
| DNase 1 0.1 ng/ml | 29 |
| DNase 1 0.01 ng/ml | 11 |
| Micrococcal Nuclease 50 U/ml | 72 |
| Micrococcal Nuclease 10 U/ml | 65 |
| Micrococcal Nuclease 2 U/ml | 50 |
| Micrococcal Nuclease 0.4 U/ml | 0 |

The results shown in Table 3 indicate that neither pool could digest DNA, in contrast to the commercially available nucleases tested in parallel. The sensitivity of the assay is demonstrated by the fact that DNase I at only 0.1 ng/ml and micrococcal nuclease at 2 U/ml gave clearly detectable signals. Therefore, it is unlikely that a contaminating nuclease accounts for the ability of the protease preparations to activate DNA fragmentation in isolated nuclei. In order to determine if the DNA fragmenting activity is mediated by the DK120-binding protease, this enzyme was purified to homogeneity and tested.

Figure 7:
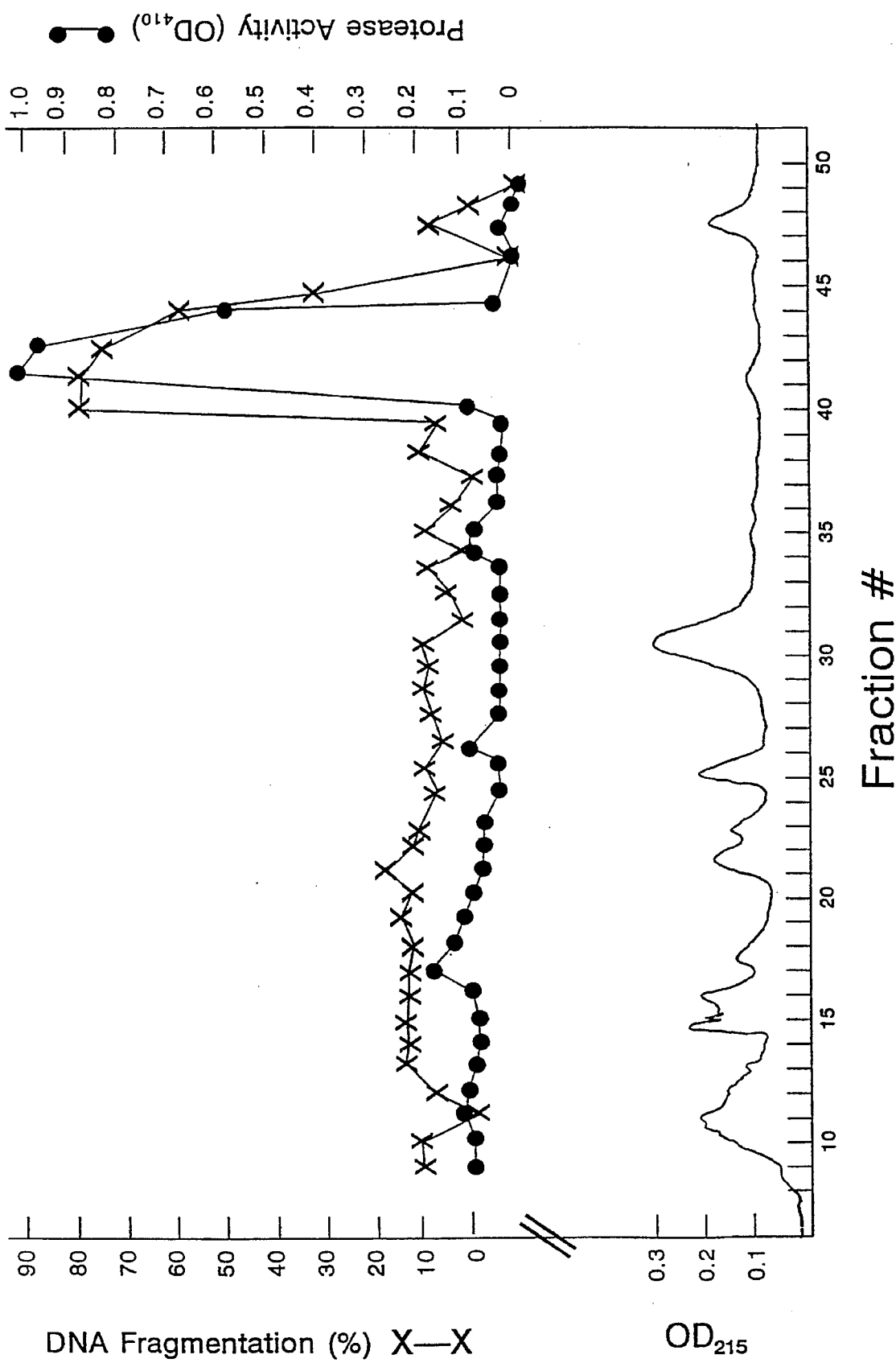
FIG. 7 shows the purification of U937 protease by reverse phase HPLC and demonstration of proteolytic and DNA fragmentation activity. Fraction numbers from the final purification step by reverse phase C4 HPLC are shown on the lower axis of FIG. 7. The lower tracing reflects the total protein profile as detected by absorbance at 215 nm. Percent DNA fragmentation (against isolated U937 nuclei) for each fraction is indicated by X's in FIG. 7, while protease activity against the MAAPV substrate for each fraction is indicated by solid circles.
Figure 8:
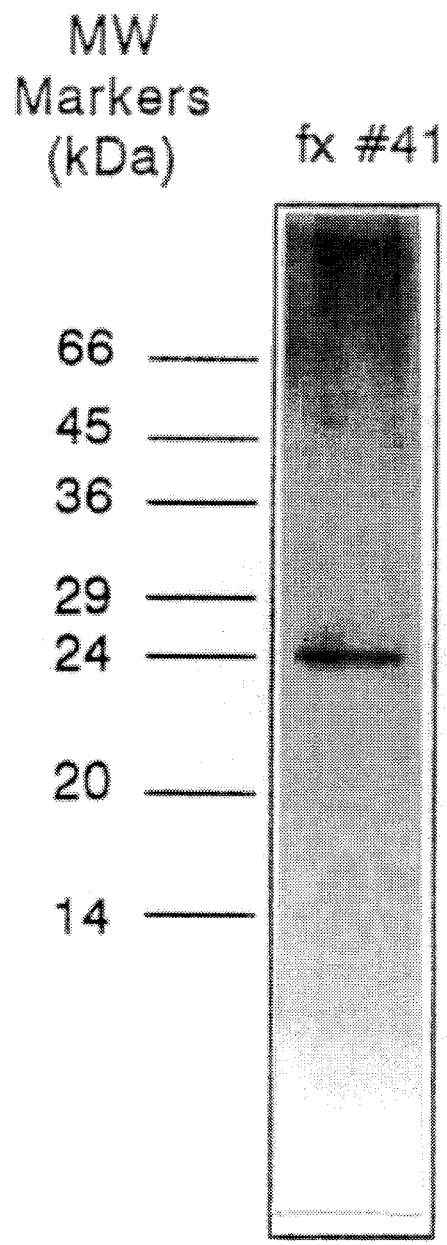
FIG. 8 is a non-reducing, silver-stained, SDS PAGE analysis of purified 24 kDa U937 protease. Molecular weight markers (in kDa) are indicated.

Protease from 5×10$^{10}$ U937 cells pretreated with UV light was purified by multiple separations on the DK120 affinity column. Active eluted fractions were pooled and applied to a heparin-Sepharose column. All protease activity bound to the column and was eluted with a NaCl gradient. Active fractions were further purified using an HPLC reverse phase C4 column. All fractions were tested for protease activity against MAAPV substrate as well as the ability to activate DNA fragmentation in isolated U937 nuclei. The results in FIG. 7 show that both activities co-eluted with a peak of activity in fraction 41. These fractions were inactive against the trypsin substrate, BLT. SDS PAGE analysis of fraction 41 under non-reducing conditions revealed a single band of 24 kDa by silver staining, as shown in FIG. 8. The molecular weight under reducing conditions was also 24 kDa. The purified enzyme was highly unstable, in that all activity was lost after 48 h at 4° C.

The results of the protease purification are summarized in Table 4.

TABLE 4

Purification of 24 kDa U937 Protease

| Purification Step | Total Protein (mg) | Protease Activity (U/ml) | Total Protease (U) | Specific Activity (U/mg) |
|---|---|---|---|---|
| Cell Lysate | 245 | not determined | n.d. | n.d. |
| DK120 Affinity | 4.10 | 27.6 | 4960 | 1210 |
| Heparin Sepharose | 0.14 | 38.9 | 777 | 5557 |
| RP HPLC | 0.0018 | 95 | 507 | 28167 |

An attempt to determine the N-terminal amino acid sequence of the reverse phase purified material was unsuccessful, due to a blocked N terminus. The amino acid composition was determined at the Stanford University Medical Center Protein and Nucleic Acid Facility using a Beckman 6300 analyzer according to standard procedures, and is shown in Table 5.

TABLE 5

Amino Acid Composition

| Residue | # Residues/Molecule |
|---|---|
| Asx | 25 |
| Thr | 7 |
| Ser | 15 |
| Glx | 30 |
| Pro | 6 |
| Gly | 43 |
| Ala | 17 |
| Val | 16 |
| Met | 3 |
| Ile | 10 |
| Leu | 22 |
| nleu | 39 |
| Tyr | 5 |
| Phe | 8 |
| His | 7 |
| Lys | 8 |
| Trp | not determined |
| Arg | 13 |

According to the present invention, a 24 kDa protease is involved in activating DNA fragmentation in U937 cells undergoing apoptosis. Evidence for the involvement of the 24 kDa protease is: a) DNA fragmentation in U937 and several other cell lines is blocked by the protease inhibitors, TPCK and DK120, b) activation of apoptosis by UV light caused approximately a 10 fold increase in the activity of a protease isolated by binding to DK120 affinity columns, and c) purification to homogeneity revealed a single peptide of 24 kDa that had protease activity and also activated DNA fragmentation in isolated U937 nuclei.

These findings provide the basis for a model of the mechanism of apoptosis in U937 cells. We propose that normal U937 cells contain the 24 kDa protease in an inactive proenzyme form or else in an active form that is normally sequestered from its substrate. This is supported by the observation that DNA fragmentation in U937 cells triggered by TNF or UV light is not blocked by inhibitors of protein synthesis. Low levels of a DK120-binding protease were recovered from normal U937 cells. This may be due to the artifactual activation of a proenzyme during cell lysis and purification. Alternatively, it may reflect the low incidence of apoptosis occurring spontaneously in cell culture.

Agents inducing apoptosis, such as UV light, may directly or indirectly activate the 24 kDa protease. UV light can cause structural modifications in proteins, and thus may activate a latent form of the 24 kDa protease. Alternatively, UV light may inactivate a protease inhibitor that would normally function to protect a cell from apoptosis. If the UV effect is indirect, the signal could be transduced by second messengers that activate the protease (or inactivate the postulated protease inhibitor). Such signals could involve protein phosphorylation, since UV light has been shown to activate certain protein kinases participating in the UV response in other cells, Devary, Y., et al. (1992) Cell 71, 1081–1091, and ionizing irradiation activates protein kinases leading to apoptosis in B lymphocytes, Uckun, F. M., et al. (1992) Proc. Natl. Acad. Sci. 89:9005–9009. Alternatively, the UV signal may be transduced through the generation of free radicals, which modify the function of many proteins.

Once activated, the 24 kDa protease acts on a substrate located in the nucleus. One possible substrate is a fragmentation-causing endonuclease that would normally be latent in the nucleus. Alternatively, the protease may cleave other molecules that in turn activate endogenous nucleases. One possible candidate is the nuclear enzyme poly-ADP-ribose polymerase (pADPRp). This enzyme is activated in cells undergoing apoptosis and its inhibitors block DNA fragmentation in U937. pADPRp is proteolytically cleaved yielding enzymatically active fragments in cells undergoing apoptosis induced by chemotherapeutic drugs as described in Kaufmann, S. H., et al. (1993) Cancer Res. 53, 3976–3985.

Previous studies have observed both generalized proteolysis as well as specific proteolytic processing of precursor IL-1 in cells undergoing apoptosis (Kaufmann, S. H. (1989) Cancer Res. 49, 5870–5878 and Hogquist, K. A., et al. (1991) Proc. Natl. Acad. Sci. 88, 8485–8489). However, in these studies, experiments were not performed to address the question of whether the protease activity is an essential step in the apoptotic pathway or is just an epiphenomenon. More recently, it has been shown that overexpression of recombinant IL-1$\beta$ converting enzyme (ICE) induced apoptosis in rat fibroblasts (Miura, M., et al. (1993) Cell 75:653–669), implicating this protease in signalling DNA fragmentation. ICE is a cysteine protease consisting of two active subunits of MW 20 and 10 kDa (Thornberry, N. A., et al. (1992) Nature 356:768–774) that requires Asp at the $P_1$ site (Howard, A. D., et al. (1991) J. Immunol. 147:2964–2969), thus differentiating it from the protease of the present invention. Since proteolytically active ICE was isolated from the cytosol of monocytes and the monocyte line, THP.1 (Kostura, M. J., et al. (1989) Proc. Natl. Acad. Sci. 86:5227–5231), it appears that synthesis of this protease is not sufficient to induce apoptosis in any cell line.

Other studies using protease inhibitors have implicated a role for proteolysis in apoptosis. For example, it has been suggested that TPCK inhibits chemotherapeutic drug-induced apoptosis in HL-60 cells (Bruno, S., et al. (1992) Leukemia 6, 1113–1120).

The effects of protease inhibitors have implicated the involvement of a serine protease in TNF-mediated tumor cell lysis (Suffys, P., et al. (1988) Eur. J. Biochem. 178, 251–256; Ruggiero, V., et al. (1987) Cell. Immunol. 107, 317–325), although these studies did not differentiate between TNF-induced necrosis or apoptosis.

Evidence from a recent study of the effect of a variety of protease inhibitors on T lymphocyte apoptosis induced by antibodies against the T cell receptor suggested two proteases may be involved (Sarin, A., et al. (1993) *J. Exp. Med.* 178, 1693–1700). One was postulated to be calpain or some other cysteine protease, whereas the other appeared to be a serine protease inhibited by DFP or PMSF. Although the U937 response was not inhibited by DFP or PMSF, it is not conclusive that the two serine proteases are different since the previous study did not isolate and characterize the T lymphocyte enzyme (Sarin, A., et al., supra). Taken altogether, these findings raise the possibility that apoptosis signal transduction may involve a proteolytic cascade. Indeed, we have unpublished evidence for activation of multiple proteases that cleave substrates different from the elastase-like substrate preferred by the 24 kDa protease from apoptotic U937 cells.

Recent progress in several laboratories studying the mechanism of cell-mediated cytotoxicity (CMC) has led to the discovery of several proteases that may be involved in apoptosis. According to the granule-exocytosis model of CMC (as reviewed in Bleackley, R. C., et al. (1988) *Immunol. Rev.* 10, 5–19 and Jenne, D., et al. (1988) *Curr. Top. Microbiol. Immunol.* 140, 33–47), after recognition of the target cell, the effector cell (cytoxic T lymphocyte (CTL) or NK cell) releases cytoplasmic granules that contain lytic mediators including cytolysin and a family of serine proteases (granzymes). Cytolysin is a pore-forming molecule that may act to promote the entry of the proteases into the target cell. Recent studies have shown that in the presence of cytolysin, or using detergent-permeabilized target cells, purified granzyme A/fragmentin 1 and fragmentins 2 and 3 can activate DNA fragmentation (Hayes, M. P., et al. (1989) *J. Exp. Med.* 170, 933–946; Shi, L., et al. (1992) *J. Exp. Med.* 176, 1521–1529; and Shi, L., et al. (1992) *J. Exp. Med.* 175, 553–556). However, the characteristics of these enzymes, summarized in Table 6, indicate they are clearly distinct from the protease of the present invention. Granzyme B and fragmentin 2 cleave tripeptide thiobenzyl ester substrates after aspartic acid. The protease of the invention is not closely related to human granzyme B since the latter is inactive on methoxysuccinyl-ala-ala-pro-val-thiobenzyl ester, a substrate preferred by elastase-like enzymes, Poe, M. P., et al. (1991) *J. Biol. Chem.* 266: 98–103. Granzyme A/fragmentin 1 and fragmentin 3 are tryptases that cleave the BLT substrate. However, the U937 protease is inactive on the BLT substrate while mediating high activity on a synthetic substrate preferred by elastase-like enzymes. U937 cells are known to contain high levels of leukocyte elastase that can be isolated in two MW forms of 30 and 60 kDa, Senior, R.M., et al. (1982) *J. Clin. Invest.* 69: 384–393. In addition to the molecular weight differences, the fact that commercially available leukocyte elastase cannot induce DNA fragmentation in U937 nuclei (FIG. 6A) indicates the protease of the present invention is not identical to leukocyte elastase. Thus, as summarized in Table 5, the 24 kDa U937 protease is distinct from proteases implicated as inducers of DNA fragmentation.

TABLE 6

The U937 Protease Differs from Leukocyte Elastase and Other Proteases Implicated as Inducers of DNA Fragmentation

| Protease | Source | MW | Substrate | Homolog | Ref. |
| --- | --- | --- | --- | --- | --- |
| Granzyme A/ Hanakah factor | Human CTL | 30 kDa reduced 60 kDa non-reduced | BLT | Fragmentin 1 | Hayes, M.P., et al. (1989) J. Exp. Med. 170, 933–946 |
| CC P1/Granzyme B | Murine CTL | 35 kDa reduced | Asp-ase | Fragmentin 2 | Lobe, C.G., et al. (1986) Proc. Natl. Acad. Sci. 83, 1448–1453 |
| Fragmentin 1 | Rat NK Cell | 30 kDa reduced | BLT | Granzyme A | Shi, L., et al. (1992) J. Exp. Med. 176, 1521–1529 |
| Fragmentin 2 | Rat NK Cell | 31 kDa non-reduced | Asp-ase | CCP1/ Granzyme B | Shi, L., et al. (1992) J. Exp. Med. 175, 553–556 |
| Fragmentin 3 | Rat NK Cell | 27 kDa non-reduced | BLT | Granzyme 3 | Shi, L., et al. (1992) J. Exp. Med. 176, 1521–1529 |
| 24 kDa Protease | Human U937 Cells | 24 kDa reduced or non-reduced | ala—ala— pro—val | | |
| Leukocyte Elastase | Human U937 Cells | 30 kDa reduced 60 kDa reduced | ala—ala— pro—val | | Poe, M.P., et al. (1991) J. Biol. Chem. 266, 98–103 |
| ICE | Monocytes | 10 and 20 kDa subunits | IL-1β at $Asp^{116}$ $Ala^{117}$ | None | Thornberry, N.A., et al. (1992) Nature 356:768–774 and Howard, A.D., et al. (1,991) J. Immunol. 147:2964–2969 |

The present invention provides substantially full length polypeptides having the 24 kDa protease activity described herein. In addition, the present invention provides for biologically active fragments of the polypeptides, or analogs or homologs thereof, including organic molecules which simulate the interactions of the peptides. Significant biological activities include protease activity, DNA fragmentation activity, and ligand binding activity. As used herein, "ligand" means a molecule that is recognized by a particular protease. The agent bound by or reacting with the protease is called a "ligand", a term which is definitionally meaningful only in terms of its counterpart protease. The term "ligand" does not imply any particular molecular size or other structural or compositional feature other than that the substance in question is capable of binding or otherwise interacting with the protease. Also, a "ligand" may serve either as the natural ligand to which the protease binds or interacts, or as a functional analogue that may act as an agonist or antagonist. Thus, the present invention provides methods for the affinity purification of ligands that interact with the protease.

Ligands that can be investigated by this invention include but are not restricted to, agonists and antagonists for proteases, toxins and venoms, viral epitopes, hormones, sugars, cofactors, peptides, enzyme substrates, cofactors, drugs, and proteins.

Transfected cells may be used as a model for studying apoptosis. For controlled investigation, mammalian cells lacking the 24 kDa protease may be transfected with an expression construct encoding the 24 kDa protease of the invention. Cells are produced that encode the protease that is often functionally equivalent to the wild-type protease. Thus, the binding properties of protease ligands may be analysed, including naturally occurring and synthetic ligands. The transfected cells find particular use for the identification of ligands having pharmaceutical efficacy. Transfected cells may be contacted with a putative drug agent, and the amount of apoptosis modulation determined, as compared to the control cells in the absence of the putative drug. Ligands identified according to the invention find a variety of uses, including modulators of apoptosis, inhibitors of neurodegenerative diseases, tumors, viral diseases, and identification of tumor promoters.

The present invention also provides for other polypeptides comprising fragments of the protease of the invention and polypeptides substantially homologous thereto. The protease peptides of the invention will generally exhibit at least about 80% homology with naturally occurring sequences of the 24 kDa protease, typically at least about 85% homology, and more usually at least about 97% homology. The length of comparison sequences will generally be at least about 16 amino acid residues, usually at least about 20 residues, more usually at least about 24 residues, typically at least about 28 residues, and preferably more than about 35 residues.

The present invention also includes fusion polypeptides between the 24 kDa protease and other proteins. For example, homologous polypeptides may be fusions with other proteases, or other apoptosis-modulating proteins, resulting in fusion proteins having mixed functionalities. Similarly, fusions may be generated with heterologous proteins, for example a reporter polypeptide, e.g. bacterial beta-galactosidase, trpE, protein A, beta-lactamase, alpha amylase, alcohol dehydrogenase, and yeast alpha mating factor.

Such polypeptides may also have amino acid residues which have been chemically modified by phosphorylation, sulfonation, biotinylation, or the addition of other moieties. In some embodiments, the modification will be useful labelling reagents, or serve as purification targets, for example, affinity ligands.

Fusion polypeptides will typically be made by either recombinant nucleic acid methods or by synthetic polypeptide methods, as are generally described in Sambrook et al., supra; Merrifield (1963) *J. Amer. Chem. Soc.* 85: 2149–2156, Merrifield (1986) *Science* 232: 341–347, and Atherton et al. (1989) *Solid Phase Peptide Synthesis: A practical approach* IRL Press, Oxford.

The nucleic acid compositions of the invention will generally be in RNA or DNA forms, mixed polymeric forms, or any synthetic nucleotides structure capable of binding in a base-specific manner to a complementary strand of nucleic acid. An example of a suitable synthetic nucleotide structure is peptide nucleic acids, as described in Nielson, P. E., et al. *Science* (1991) 254:1497–1500. The described nucleic acid embodiment is typically derived from genomic DNA or cDNA, prepared by synthesis, or derived from combinations thereof. The DNA compositions generally include the complete coding region encoding the 24 kDa protease, or fragments thereof, e.g. comprising at least 8 codons, usually at least 12 codons, or usually at least about 15codons, typically at least about 20 codons, more typically at least about 30 codons and preferably even more. One or more introns may be present.

The nucleic acids encoding the 24 kDa protease may be used to prepare an expression construct for the 24 kDa protease. The expression construct normally comprises one or more DNA sequences encoding the 24 kDa protease operably linked and under the transcriptional control of a native or other promoter. Usually the promoter will be a eukaryotic promoter for expression in a mammalian cell. The transcriptional regulatory sequences will typically include a heterologous promoter or enhancer which is recognized by the host cell. The selection of an appropriate promoter will depend on the host cell. Examples of suitable promoters include trp, lac, phage promoters, tRNA promoters, and glycolytic enzyme promoters. Convenient expression vectors are commercially available.

The expression construct will often be contained in a vector capable of stable extrachromosomal maintenance in an appropriate cellular host or may be integrated into the host genome. As used herein, "host" or "host cell" includes any suitable prokaryotic or eukaryotic cell. The expression construct may be bordered by sequences which allow for insertion into a host, such as regions of homology for homologous recombination, transposon sequences, lysogenic viral sequences, and the like. Normally, the expression construct additionally includes cis or trans markers, preferably cis markers, for selection of host cells containing the construct. In mammalian cells, the protease gene itself may provide a convenient marker. However, in prokaryotic host cells, markers such as resistance to a cytotoxic agent, complementation of an auxotrophic host to prototrophy, production of a detectable product, and the like, may be more convenient.

Polyclonal and/or monoclonal antibodies to the protease of the present invention may be prepared. The gene or synthetic peptide fragments thereof may be prepared as described herein, and coupled to a carrier molecule, for example keyhole limpet hemocyanin, and injected into rabbits at selected times over several months. The rabbit sera may be tested for immunoreactivity to the protease or fragments thereof. Monoclonal antibodies may be made by injecting mice with the protease or synthetic peptide fragments thereof. Monoclonal antibodies may be screened by methods known in the art, as are described, for example, in Harlow and Lane (1988) *Antibodies: A laboratory manual*, Cold Spring Harbor Press, New York, and Goding (1986) *Monoclonal antibodies: Principles and Practice* (2d ed.) Academic Press, New York. The antibodies will be tested for specific immunoreactivity with an epitope of the protease. These antibodies will find use in diagnostic assays or as an active ingredient in a pharmaceutical composition.

For production of polyclonal antibodies, an appropriate target immune system is selected, typically a mouse or rabbit, although other species such as goats, sheep, cows, guinea pigs, and rats may be used. The substantially purified antigen is presented to the immune system according to methods known in the art. The immunological response is typically assayed by an immunoassay. Suitable examples include ELISA, RIA, fluorescent assay, or the like. These antibodies will find use in diagnostic assays or as an active ingredient in a pharmaceutical composition.

The compositions of the present invention have utility for modulating the growth and differentiation of cells through the apoptotic process. Modulation of the apoptotic process includes deceleration of the rate of apoptosis in a population of cells, or elimination of the cellular apoptotic response to apoptosis inducing agents. Modulation of the apoptotic process also includes induction or acceleration of apoptosis where it is desirable to increase the rate of cell death or to specifically target a population of cells. For example, the induction of apoptosis in tumor cells or in other cells showing increased proliferation and growth provides an effective therapy to decrease or abolish the growth of these cells. The compounds of the present invention also have utility in combatting drug resistance, which is a common problem with current cancer treatments. Drug resistance may be a resistance to apoptosis in general, and thus, the proteases of the present invention may be used to decrease drug resistance. In this embodiment, the compounds of the invention may be used in conjunction with other antineoplastic agents. Mechanisms of drug resistance are described, for example, in Remington's Pharmaceutical Sciences, 18th Edition, supra. In some embodiments, the compositions of the invention may be used to assay tissue injury and regeneration. A suitable model system for the assay of tissue injury is the thymus of dexamethasone treated rats, as described in Schwartzman, Robert et al. (1991) *Endocrinology* 128:2 1190–1197, the contents of which are hereby incorporated by reference.

The compositions of the present invention thus have utility for a variety of therapeutic indications, including as anti-viral, anti-microbial, or anti-parasitic agents, as neoplastic agents for the treatment of acute lymphoblastic or myeloid leukemia, chronic myeloid, myelogenous, granulocytic, or lymphatic leukemia, acquired immune deficiency syndrome (AIDS), neurogenerative diseases, myelodysplatic syndrome, Hodgkin's lymphoma, malignant lymphomas such as non-Hodgkin's lymphoma, or Burkitt's lymphoma, neoplasms and the like.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics*, 7th Edition (1985), MacMillan Publishing Company, New York, and *Remington's Pharmaceutical Sciences* 18th Edition, (1990) Mack Publishing Co, Easton Penn. Methods for administration are discussed therein, including oral, intravenous, intraperitoneal, intramuscular, transdermal, nasal, iontophoretic administration, and the like.

The pharmaceutical compositions may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated-or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention will now be further described by references to the following experimental examples, which are intended to be exemplary, and not scope-limiting.

EXAMPLE 1. CELL LINES AND REAGENTS

The human histiocytic lymphoma, U937, the human mammary carcinoma BT-20, the human myelocytic leukemia HL-60, and the murine fibroblast cell line 3T3 were obtained from the ATCC (Rockville, MD). All cell lines were maintained in antibiotic-free RPMI 1640 supplemented with 10% FCS and l-glutamine (2 mM). All cell lines were routinely tested for mycoplasma and always found to be negative according to the Mycotect kit (GIBCO, Grand Island, N.Y.).

Purified human rTNF (specific activity=$1\times10^7$ U/mg) was purchased from R&D Systems, Minneapolis, Minn. DNase I was purchased from Worthington (Freehold, N.J.), micrococcal nuclease (116 U/mg) was from Calbiochem (San Diego, Calif.). All substrates for the protease assays and protease inhibitors (except DK120) were purchased from Sigma (St. Louis, Mo.). DK120 was prepared as described in Example 7. Trypsin and chymotrypsin were obtained from Sigma, and human leukocyte elastase was obtained from Calbiochem.

EXAMPLE 2. DNA FRAGMENTATION ASSAY

DNA fragmentation assays were carried out according to the protocol of Wright, S. C., et al. (1992) *J. Cell. Biochem.* 48, 344–355. Target cells were labeled with $^3$H-thymidine and plated in triplicate in flat bottom microtiter plates. Cells were incubated for the indicated length of time for each experiment in the presence of TNF or various inhibitors. In some experiments, cells were treated with UV light at 245 nm using a UV Crosslinker (Fisher Scientific). Assays were harvested and counted on a Packard matrix 96 beta counter. Percent DNA fragmentation was calculated as for the nuclear assay described in Example 3. In assays to test the effects of various inhibitors, the pH of extra wells containing assay buffer, target cells, and each inhibitor was always checked at the beginning and end of each assay to assure that the pH remained at 7.5.

EXAMPLE 3. DNA FRAGMENTATION ASSAY USING U937 NUCLEI TARGETS

U937 cells were labeled with $^3$H-thymidine by culturing overnight with isotope at 0.5 μCi/ml. The cells were pelleted, washed once, and the cytoplasmic membrane lysed by resuspending the cells in assay buffer (50 mM Tris, 250 mM sucrose 10 mM MgSO$_4$, pH 7.5) plus 0.02% NP-40. Nuclei were then pelleted and resuspended in assay buffer at $1\times10^6$/ml. The assay was set up in triplicate in flat bottom microtiter plates under sterile conditions. Nuclei (0.05 ml) were mixed with 0.05 ml of sample diluted in 50 mM Tris pH 7.5 or buffer alone to determine total counts. Plates were incubated for 5 h at 37° C. and then harvested by the addition of 0.1 ml of harvesting buffer (10 mM Tris, 10 mM EDTA, 0.3% Triton X-100, pH 7.5). Plates were harvested by filtration onto glass fiber paper and counted on a Packard Matrix 96 beta counter. Percent DNA fragmentation was calculated as follows:

$$\frac{\text{total cpm} - \text{test cpm}}{\text{total cpm}} \times 100$$

EXAMPLE 4. VISUALIZATION DNA FRAGMENTATION BY GEL ELECTROPHORESIS

DNA fragmentation was carried out according to the procedure of Example 2. After the desired treatments, the cells were lysed and debris was removed by centrifugation at 13,000 xg for 10 sec. DNA in the supernatant was ethanol precipitated after phenol extraction. Equivalent amounts of material from a fixed number of cells were loaded and electrophoresed on a 1.0% agarose slab gel. DNA was visualized by ethidium bromide staining.

EXAMPLE 5. VISUALIZATION OF DNA FRAGMENTATION IN U937 CELL LINE TARGET NUCLEI

DNA fragmentation was carried out according to the procedure of Examples 2 and 3. The assay was adapted to assess the effects of compounds on DNA fragmentation in isolated nuclei. Nuclei were prepared from normal unlabeled U937 cells as described in Example 3. After the desired treatments of aliquots of $5 \times 10^6$ nuclei, 1.0 ml of harvesting buffer (see Example 3) was added and debris was removed by centrifugation at 13,000 xg for 10 sec. DNA in the supernatant was ethanol precipitated after phenol extraction. Equivalent amounts of material from a fixed number of cells were loaded and electrophoresed on a 1.0% agarose slab gel. DNA was visualized by ethidium bromide staining.

EXAMPLE 6. NUCLEASE ASSAY WITH U937 DNA AS SUBSTRATE $^3$H-thymidine-labeled DNA was prepared by incubating U937 cells with isotope at 0.5 µCi/ml for 24 h. The cells were washed and DNA was isolated according to the procedure of Sambrook, J., et al. (1989) *Molecular Cloning*, Cold Spring Harbor Laboratory Press, N.Y., vol. 2, p. 9.22. $^3$H-labeled U937 DNA was diluted to 75 µg/ml in 50 mM Tris, 10 mM MgSO$_4$, 1 mM CaCl$_2$, pH 7.5. 0.05 ml of substrate and 0.05 ml of sample were mixed in Eppendorf tubes and incubated at 37° C. for 20 h. The assay was terminated by the addition of 0.05 ml of 0.5% BSA plus 0.05 ml of 7% perchloric acid and placed on ice for 15 min. The intact DNA was pelleted by centrifugation at 13,000xg for 15 min and the radioactivity in 0.1 ml of the supernatant assessed by scintillation counting. The % DNA fragmentation was calculated as the measured cpm in the supernatant divided by the total cpm of the original DNA added ×100.

EXAMPLE 7. PROTEASE ASSAYS

Proteolytic activity was assayed using synthetic substrates selective for different known proteases. All assays were set up by adding 0.02 ml of sample (or known enzyme as a positive control) plus 0.18 ml of appropriate substrate dissolved in PBS PH 7.5 in triplicate in flat bottom microtiter plates, incubated for the indicated length of time at room temperature, and the OD at 405 nm measured using a plate reader.

To measure chymotrypsin-like activity, N-succinyl-ala-ala-pro-phe p-nitroanilide (SAAPP) at 0.1 mM was used as the substrate. Trypsin-like activity was measured using N-α-benzyloxycarbonyl-L-lysine thiobenzyl ester (BLT) at 0.2 mM plus 0.11 mM nitrobenzoic acid.

Elastase-like activity was measured using N-methoxysuc-cinyl-ala-ala-pro-val p-nitroanilide (MAAPV) at 0.25 mM as a substrate. For convenience and maximum sensitivity, these assays were routinely incubated 20 h to monitor protease purification. Under these conditions, the elastase dose response was linear up to a concentration of 6.0 µg/ml (OD of 1.0), see FIG. 3C. The activity of the protease samples tested during purification did not exceed an OD of 1.0 under these assay conditions. In order to quantitate the activity of the purified protease, identical assays were set up but kinetic readings of OD were taken every hour from 1–6 h. One unit of enzyme was calculated as the amount of enzyme that hydrolyzes 1.0 nM substrate/h.

EXAMPLE 8. PREPARATION OF THE DK120 AFFINITY RESIN

The synthesis and characterization of the boronic acid amino acid analog protease inhibitor (DK120) as well as the non-inhibitory boronic acid compound, IBA, was as described in Kinder, D. H., et al. (1985) *J. Med. Chem.* 28 1917–1925, and Kinder, D. H., et al. (1991) *Invasion and Metastasis* 12 309–319. DK120 is a tripeptide reversible inhibitor of chymotrypsin (carbobenzoxy-ala-ala-borophe) in which a boronic acid is in place of COOH at the site of enzymatic serine OH attack. Affinity resin was prepared in a manner similar to that described in Emod, et al. (1978) *Affinity Chromatography* ed. Hoffman-Ostenkof, O. et al. Pergamon Press, UK pp. 123–128, and Billings, P. C., et al., (1988) *Cancer Res.* 48, 1798–1802, except that epoxy activated Sepharose 6B was used instead of cyanogen bromide activated resin, Sundberg, L., et al. (1974) *J. Chromatogr.* 90, 87–98. DK120 was N-de-blocked by hydrogenation in the presence of 5% Pd/carbon (10% weight) in 95% ethanol. Catalyst was removed by filtration through celite, and the ethanol was evaporated. The resulting oily residue was dried under vacuum for at least 1 h to remove excess alcohol. The de-protected product was dissolved in dimethylformamide (DMF) for coupling to the resin. Sepharose 6B (Sigma) was swollen with water, then reacted with DK120 at pH 10 in 0.1M NaOH/DMF (1:1) for 16–24 h at 37° C. The resin was subsequently washed with DMF, followed by water. The derivatized resin was then treated with 1M ethanolamine at room temperature for 4 h. The resin was then rinsed sequentially with water, acetate buffer, pH 4.0, and finally with borate buffer, pH 8.0. The affinity resin was stored in 20% ethanol prior to use. A control resin was prepared that lacked the DK120 ligand but was treated with ethanolamine and washed as described above.

EXAMPLE 9. PREPARATION OF CELL LYSATES FOR PROTEASE PURIFICATION

Normal or UV light-treated (0.2 J/cm$^2$ in a UV Crosslinker) cells were pelleted and resuspended at $2 \times 10^8$/ml in ice cold lysing buffer (50 mM Tris, 0.3% NP-40, pH 7.0). The debris was pelleted by centrifugation in a microfuge at 14,000xg for 15 min. The supernatant was used immediately or stored at −70° C. until further purification.

EXAMPLE 10. DK120 AFFINITY CHROMATOGRAPHY

One ml of affinity resin was equilibrated with starting buffer (50 mM Tris pH 7.5, 100 mM NaCl, 1.0 mM $CaCl_2$, 0.1% $NAN_3$, and 0.05% Tween 20). Cell lysate was mixed with the resin and allowed to bind for 60 min. The column was then washed with starting buffer at 0.5 ml/min until the $OD_{280}$ returned to baseline. Bound material was eluted with starting buffer plus 0.1% HCl pH 4.5. During elution, 1.0 ml fractions were collected and immediately neutralized to pH 7.5. The column was regenerated by washing with 2.0M NaCl (no additional protease was eluted during this step).

EXAMPLE 11. HEPARIN SEPHAROSE AFFINITY CHROMATOGRAPHY

Heparin Sepharose (Pharmacia) was equilibrated in starting buffer (50 mM Tris pH 7.5, 1.0 mM $CaCl_2$, 0.05% Tween 20, 0.1% $NAN_3$). Active fractions eluted from the DK120 column were applied followed by washing with starting buffer at 0.5 ml/min until the $OD_{280}$ returned to baseline. Bound material was eluted with a linear gradient from 0 to 2.5M NaCl in starting buffer. One ml fractions were collected and tested for protease activity. All flow-through fractions were negative for protease activity whereas proteases showing activity against the MAAPV substrate eluted at 1.0–1.5M NaCl.

EXAMPLE 12. REVERSE PHASE (RP) HPLC

Separations were performed on a Waters 625 liquid chromatography system using a 3 cm×2.1 mm C4 cartridge (Brownlee). Buffer A was water plus 0.1% trifluoroacetic acid and buffer B was 80% 2-propanol plus 0.1% trifluoroacetic acid. Bound material was eluted using a linear gradient from 75%A/25%B to 35%A/65%B over 60 min at a flow rate of 0.2 ml/min. 0.2 ml fractions were collected and immediately neutralized to pH 7.5. All fractions were tested for protease activity as well as nuclear DNA fragmenting activity.

EXAMPLE 13. SDS PAGE

Protease purity was assessed using 15% Laemmi SDS gel electrophoresis followed by silver staining using the Daiichi II kit (ISS, Hyde Park, Mass.). Protease was purified from UV light-treated U937 cells and the active fraction #41 from the RP separation shown in FIG. 7 was analyzed by SDS PAGE under non-reducing conditions, revealing a 24 kDa band. Identical results were observed under reducing conditions.

The foregoing description of the preferred embodiments of the invention has been presented for purposes of illustration and description. They are not intended to be exhaustive or to limit the invention to the precise form disclosed, and many modifications and variations are possible in light of the above teaching.

The references discussed herein are provided solely for their disclosure prior to the filing date of the present application. Nothing herein is to be construed that the inventors are not entitled to antedate such disclosure by virtue of prior invention.

All publications, patents, and patent applications herein are incorporated by reference to the same extent as if each individual publication, patent, or patent application was specifically and individually indicated to be incorporated by reference.

Such modifications and variations which may be apparent to a person skilled in the art are intended to be within the scope of this invention.

What is claimed is:

1. A process for isolating and purifying an apoptotic protease from mammalian cells, the process comprising the steps of
    a) preparing a cytoplasmic extract of mammalian cells pretreated with an apoptosis-inducing agent;
    b) applying the extract to an affinity column having an immobilized DK120 protease inhibitor;
    c) eluting a protease containing fraction from the affinity column;
    d) applying the protease containing fraction to a heparin-sepharose column; and
    e) eluting a fraction having protease activity with a NaCl gradient to obtain a substantially pure apoptotic protease.

2. The process of claim 1, wherein the apoptosis inducing agent is selected from the group consisting of UV light, hyperthermia, heat shock, calcium, ATP, actinomycin D, A23187 $Ca^{2+}$-$Mg^{2+}$ ionophore, cytochalasin B, cycloheximide, anti-CD3/T-cell receptor antibodies, epipodophyllotoxins, gliotoxin, glucocorticoids, lymphotoxins, RU486, TCDD, TGF-β1, oxidative stress, viral infections, chemotherapeutic drugs, cold shock, gamma radiation, cisplatin, etoposide, teniposides, DNA alkylating agents, macromolecular synthesis inhibitors, natural killer cells, effector cells, lymphotoxins, K cells and T cells.

3. The process of claim 2 wherein the apoptosis inducing agent is UV light.

4. The process of claim 1 wherein eluting the protease containing fraction from the heparin-sepharose column comprises the steps of applying a linear 0 to 2.5M NaCl gradient and recovering the protease in fractions eluting at between 1.0 and 1.5M NaCl.

5. The process of claim 3 wherein the mammalian cells are U937 cells.

6. A mammalian apoptotic protease isolated according to the process of claim 1.

7. The protease of claim 6 that is 24 kDa and has the following amino acid composition expressed in number of residues per molecule: 25 asx; 7 thr; 15 ser; 30 glx; 6 pro; 43 gly; 17 ala; 16 val; 3 met; 10 ile; 22 leu; 39 nleu; 5 tyr; 8 phe; 7 his; 8 lys; 13 arg; with trp not determined.

8. An apoptotic mammalian protease of 24 kDa obtained from mammalian cells pretreated with an apoptosis-inducing agent and having the following amino acid composition expressed in number of residues per molecule: 25 asx; 7 thr; 15 ser; 30 glx; 6 pro; 43 gly; 17 ala; 16 val; 3 met; 10 ile; 22 leu; 39 nleu; 5 tyr; 8 phe; 7 his; 8 lys; 13 arg; with trp not determined.

9. The protease of claim 8 wherein the protease cleaves the peptide substrate alanine-alanine-proline-valine.

10. The protease of claim 6 wherein the protease cleaves pro-val peptide bonds.

* * * * *

UNITED STATES PATENT AND TRADEMARK OFFICE
CERTIFICATE OF CORRECTION

PATENT NO. : 5,605,826
DATED : February 25, 1997
INVENTOR(S) : Susan C. Wright et al.

It is certified that error appears in the above-identified patent and that said Letters Patent is hereby corrected as shown below:

<u>Column 1</u>,
Line 4, insert the following as first sentence after "TITLE" and before "FIELD OF THE INVENTION":

-- This invention was made, at least in part, with government support under grant number CA68223 awarded by the National Institutes of Health. The U.S. government has certain rights in the invention. --

Signed and Sealed this

Third Day of August, 2004

JON W. DUDAS
*Acting Director of the United States Patent and Trademark Office*